United States Patent

Krause et al.

[11] 4,397,791
[45] Aug. 9, 1983

[54] PROCESS FOR REACTING ALCOHOLS AND/OR PHENOLS WITH PHOSPHORUS PENTASULFIDE

[75] Inventors: Werner Krause; Jürgen Grosse, both of Hürth; Werner Klose, Erftstadt, all of Fed. Rep. of Germany

[73] Assignee: Hoechst Aktiengesellschaft, Fed. Rep. of Germany

[21] Appl. No.: 243,613

[22] Filed: Mar. 13, 1981

[30] Foreign Application Priority Data

Mar. 22, 1980 [DE] Fed. Rep. of Germany ....... 3011085

[51] Int. Cl.³ .......................................... C07F 9/165
[52] U.S. Cl. .................................................. 260/981
[58] Field of Search ...................................... 260/981

[56] References Cited

U.S. PATENT DOCUMENTS 4,083,899 4/1978 Demarcq .............................. 260/981

FOREIGN PATENT DOCUMENTS 2421462 1/1977 Fed. Rep. of Germany .
2828721 10/1980 Fed. Rep. of Germany .
1228528 4/1971 United Kingdom .
1558956 1/1980 United Kingdom .

Primary Examiner—Anton H. Sutto
Attorney, Agent, or Firm—Connolly and Hutz

[57] ABSTRACT

The invention relates to a process wherein an alcohol and/or phenol is reacted with phosphorus pentasulfide in the presence of a catalyst which is selected from
(a) phosphonium salts of the general formula:

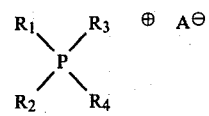

(b) ammonium salts of the general formula:

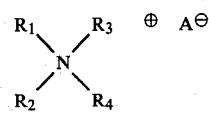

(c) phosphine oxides of the general formula:

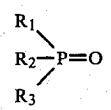

(d) phosphine sulfides of the general formula:

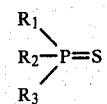

(e) phosphinic acid derivatives of the general formula:

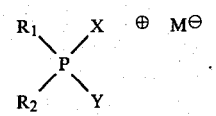

In formulae I through V, the substituents $R_1$, $R_2$, $R_3$ and $R_4$ each stand for identical or different alkyl-, aryl-, alkaryl- or aralkyl- groups having from 1 to 22 carbon atoms. A stands for an inorganic or organic acid, and X and Y, respectively, stand for both oxygen and sulfur, and M stands for a monovalent metal or oxygen.

2 Claims, No Drawings

PROCESS FOR REACTING ALCOHOLS AND/OR PHENOLS WITH PHOSPHORUS PENTASULFIDE

The present invention relates to a process, wherein an alcohol and/or phenol is reacted with phosphorus pentasulfide in the presence of a catalyst with the resultant formation of O,O-dialkyl-, O,O-diaryl- or O-alkyl-O-aryldithiophosphoric acids which find widespread uses as intermediates, especially in the production of insecticides, oil additives or flotation collectors.

The reaction of an alcohol or phenol with phosphorus pentasulfide takes place predominatly in accordance with the following equation:

$$P_4S_{10} + 8ROH \rightarrow 4(RO)_2P(S)SH + 2H_2S.$$

The resulting crude acids have a strength of about 80 to 90% only, and the reaction involves the formation of the following by-products, which are obtained in more or less important proportions:
$(RO)_2P(S)SR$; $(RO)_3PS$; $RO_2P(S)H$; $(RO)_2P(S)OH$; $(RO)_2P(S)SP(S)(OR)_2$; $(RO)_2P(S)SSP(S)(OR)_2$; and also the formation of elementary sulfur.

The by-products are customarily obtained in an overall proportion of 10 to 20% so that it is necessary for these undesirable constituents to be removed by a purifying operational step.

Substantially two processes for effecting the purifying treatment have been described, namely subjecting the crude acid to distillation under vacuum or precipitating it in salt form and successively liberating dithioacid by treatment with a strong mineral acid (cf. German Patent Specification No. 2 421 462).

As to the distillative treatment just referred to, it is technically applicable only to those products which are obtained by reacting phosphorus pentasulfide with a short chain alcohol (methanol, ethanol, n-propanol, iso-propanol). Tests based on differential thermal analysis have shown the O,O-dialkyldithiophosphoric acids to be little resistant to high temperatures. Already at about 100° C. have various derivatives been found to undergo decomposition reactions which, in one extreme case or other, may even culminate in the entire reaction mixture undergoing spontaneous decomposition. This and the relatively low boiling point make it technically good practice for the distillation to be effected only on the lower members, i.e. on the O,O-dimethyl up to O,O-dipropyldithiophosphoric acids. Even in this case, however, the yields are not higher than 80 to 85%. In addition to this, very ill-smelling and difficult-to-handle distillation residues are obtained which, for reasons of environmental protection, have to be disposed of by expensive methods.

German Patent Specification No. 2 421 462 describes a process which provides for the crude acid to be initially reacted with ammonia so as to obtain the ammonia salt. By filtration, the ammonium salt is first freed from contaminants and then reacted with a mineral acid to give pure O,O-dialkyl- or O,O-diaryldithiophosphoric acid. Needless to say, this is a complicated process which is more especially carried out with heavy expenditure of chemicals, machinery and manpower. It should be added that the distillation process and salt purification process referred to hereinabove both call for the investment of considerable capital.

As regards longer chain O,O-dialkyldithiophosphoric acids and O,O-diaryldithiophosphoric acids, it is impossible for them to be purified commercially with the use of either the distillation or salt purification process described. As a result, only acids of unsatisfactory purity have been obtained heretofore.

It has been described that by reacting phosphorus pentasulfide with an alcohol- and/or phenol mixture it is basically possible to also produce dithiophosphoric acid diesters with various ester groups. O-alkyl-O-aryldithiophosphoric acid esters are more particularly intermediate products interesting for lubricant additives. On account of the minor reactivity of the phenols, as compared with that of alcohols, the processes described heretofore produce poor yields of mixed ester only. Another method provides for equimolar mixtures of O,O-dialkyldithiophosphoric acids and O,O-diaryldithiophosphoric acids to be reacted with one another, wherein the mixed ester is obtained in yields not higher than 27 to 29 mol %, even after relatively long reaction periods (cf. British Patent Specification No. 1,558,956).

It is therefore desirable to have a process for making dithiophosphoric acids which is improved to the extent necessary to make separate purifying treatment unnecessary, i.e. which permits the production of O,O-dialkyl-, O-alkyl-O-aryl- or O,O-diaryldithiophosphoric acids by subjecting phosphorus pentasulfide to alcoholysis and/or phenolysis, the acids being obtained in yields of more than 90%, preferably more than 95%.

This has been made possible by the use of novel catalysts which permit the reaction between alcohol and phenol, respectively, with phosphorus pentasulfide to occur at an increased velocity and permit the resulting dithiophosphoric acids to be obtained in considerably increased yields.

In accordance with this invention, the novel catalysts are selected from phosphorus and nitrogen compounds which belong to the following types of compounds:

(a) phosphonium salts of the general formula:

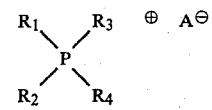   I (b) ammonium salts of the general formula:

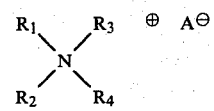   II (c) phosphine oxides of the general formula:

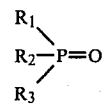   III (d) phosphine sulfides of the general formula:

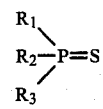   IV (e) phosphinic acid derivatives of the general formula:

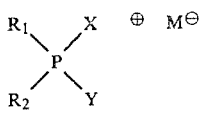

In the above formulae I through V, the substituents $R_1$, $R_2$, $R_3$ and $R_4$ each stand for identical or different alkyl-, aryl-, alkaryl-, or aralkyl groups having from 1 to 22 carbon atoms, and preferably stand for alkyl groups having from 1 to 12 carbon atoms.

A stands for the radical of an inorganic or organic acid, such as e.g. a hydrohalic acid, or sulfuric acid, nitric acid, acetic acid or a dialkyldithiophosphoric acid, X and Y, respectively, stand for both oxygen and sulfur, and M stands for a monovalent metal or for hydrogen.

The invention provides for the catalyst to be used in a proportion of 0.001 to 5 weight %, preferably in a proportion of 0.01 to 1 weight %, based on the alcohol or phenol used.

It is possible for the catalyst to be dissolved in the respective alcohol (phenol) and for the alcohol (phenol) having the catalyst dissolved therein to be continuously added to the reaction mixture. It is also possible for solid or dissolved catalyst to be added at once or portionwise to a phosphorus pentasulfide suspension; in the event of a phenol being used, it is preferable for the three components comprising phosphorus pentasulfide, catalyst and phenol to be subjected to direct en bloc reaction.

The catalysts described heretofore for alcoholysis or phenolysis of phosphorus pentasulfide have been used primarily in an attempt to increase the velocity with which the reaction between alcohol and phenol, respectively, and phosphorus pentasulfide occurs (cf. German Patent Specification "Auslegeschrift" No. 2,828,721 and British Patent Specification No. 1,228,528).

As results from tests described hereinafter, the above prior catalysts have partially been found to even impair the quality of the resulting crude acid or the acid yield.

This is in contrast with the novel catalysts which permit the reaction velocity to be increased and, at the same time, permit the yield of desirable acid to be significantly improved. This is more particularly true concerning the production of mixed alkyl-, aryl-, and alkylaryl esters. The acid yield is partially increased by more than 10%, so that it is possible to produce crude acids with a purity of more than 90% and even more than 95%, which commonly need not be subjected to any additional purifying treatment. Needless to say, this adds considerably to the commercial attractiveness of the phosphorus pentasulfide alcoholysis or phenolysis. A further technically beneficial result resides in the fact that extremely minor proportions of catalyst are necessary to provide for an optimum catalytic activity.

As can be seen from those Examples hereinafter which were carried out with the catalysts of this invention, the quantity of residual phosphorus pentasulfide obtained therein was lower than the quantity of residual phosphorus pentasulfide obtained in the comparative Examples which were carried out without, or with the use of customary, catalysts.

As results, the present catalysts permit the alcoholysis or phenolysis of phosphorus pentasulfide to occur more rapidly and also more completely than heretofore. Needless to say, this permits the capacity of the production unit to be considerably improved, as can be seen from the following reactivity test.

The reactivity of phosphorus pentasulfide was tested as follows: 50 g of $P_2S_5$ in 125 g of 2-ethylhexanol was reacted with agitation in a Dewar vessel. The starting temperature was at 30° C. After 1 hour, the temperature was found to have been increased by 26° C. A 26°/h temperature increase is typical of phosphorus pentasulfide grades of medium or high reactivity. The same test, repeated with addition of 0.06% of tetrabutylphosphonium bromide (based) on 2-ethylhexanol), produced a temperature increase of 46° C. This is a value which is typical of phosphorus pentasulfide of outstanding purity. In other words, it is possible by the addition of very minor catalyst proportions very significantly to increase the reactivity of phosphorus pentasulfide.

The following Examples show that the present catalysts enable very pure crude acids to be obtained in high yields. In the Examples describing the invention, purity and yield are always higher than 90%, and commonly higher than 95%. In other words, the present process is the first to permit the commercial production of relatively long chain O,O-dialkyldithiophosphoric acids of high purity, which incidentally cannot technically be purified by distillation or salt purification.

The following Examples illustrate the invention which is, however, not limited thereto.

EXAMPLE 1

(Without catalyst)

444 g of phosphorus pentasulfide was suspended in 140 ml of toluene in a 1-liter glass flask which was provided with a stirrer, dropping funnel, reflux condenser, thermometer and gas inlet, and the suspension was reacted therein for 2 hours, with thorough agitation, with 256 g of $CH_3OH$. The resulting hydrogen sulfide was absorbed in sodium hydroxide solution. The reaction solution was maintained for a further 30 minutes at 70° C. for post-reaction. Next, the whole was cooled to room temperature and the crude acid was treated for 1 hour with a stream of nitrogen so as to be freed from residual hydrogen sulfide. Unreacted phosphorus pentasulfide was filtered off. 721 g of a 74.9% O,O-dimethyldithiophosphoric acid solution in toluene was obtained. The dimethyldithiophosphoric acid yield was 86.8%, based on phosphorus pentasulfide which underwent reaction. The phosphorus pentasulfide residue was 7.3 g (1.6%)

EXAMPLE 1a (Invention)

The procedure was as in Example 1, but 0.13 g of $(CH_3)_4PCl$ was dissolved in methanol, prior to reaction. 739 g of an 81.3% crude acid solution in toluene was obtained. The O,O-dimethyldithiophosphoric acid yield was 95.1%, based on phosphorus pentasulfide which underwent reaction. The phosphorus pentasulfide residue was 0.5 g (0.1%). As compared with Example 1, the yield was increased by 8.3%.

EXAMPLE 1b (Invention)

The procedure was as in Example 1, but 0.38 g of trioctyl phosphine oxide was dissolved in methanol, prior to reaction. 739 g of an 80.0% crude acid solution in toluene was obtained. The O,O-dimethyldithiophosphoric acid yield was 93.7%, based on phosphorus pentasulfide which underwent reaction. The phosphorus pentasulfide residue was 1.4 g (0.3%). As compared with Example 1, the yield was increased by 6.9%.

EXAMPLE 1c (Invention)

The procedure was as in Example 1, but 0.74 g of tetrabutyl ammonium iodide was dissolved in methanol, prior to reaction. 741 g of an 81.1% crude acid solution in toluene was obtained. The O,O-dimethyldithiophosphoric acid yield was 95.2%, based on phosphorus pentasulfide which underwent reaction. The phosphorus pentasulfide residue was 0.9 g (0.2%). As compared with Example 1, the yield was increased by 8.4%.

EXAMPLE 2

(Without catalyst)

444 g of phosphorus pentasulfide was suspended in 170 g of O,O-dimethyldithiophosphoric acid (96%) and reacted within 2 hours at 60° C. with 256 g of $CH_3OH$. The resulting reaction solution was maintained for a further 30 minutes at 60° C., for post-reaction. Next, the whole was cooled to room temperature, residual $H_2S$ was expelled by means of nitrogen, and filtered. 776 g of an 86.7% crude acid solution was obtained. The O,O-dimethyldithiophosphoric acid yield was 82.7%, based on phosphorus pentasulfide which underwent reaction.

The phosphorus pentasulfide residue was 12.1 g (2.7%).

EXAMPLE 2a (Invention)

The procedure was as in Example 2, but 0.68 g of tetrabutyl phosphonium bromide was dissolved in methanol, prior to reaction. 799 g of a 96% crude acid solution was obtained. The O,O-dimethyldithiophosphoric acid yield was 95.4%, based on phosphorus pentasulfide which underwent reaction. The phosphorus pentasulfide residue was 1.2 g (0.3%). As compared with Example 2, the yield was increased by 12.6%.

EXAMPLE 2b (Invention)

The procedure was as in Example 2, but 1.6 g of trimethyl phosphine sulfide was dissolved in methanol, prior to reaction. 784 g of a 92.8% crude acid solution was obtained. The O,O-dimethyldithiophosphoric acid yield was 90.5%, based on phosphorus pentasulfide which underwent reaction. The phosphorus pentasulfide residue was 6.2 g (1.4%). As compared with Example 2, the yield was increased by 7.7%.

EXAMPLE 2c (Invention)

The procedure was as in Example 2, but 1.6 g of sodium-dimethyldithiophosphinate was dissolved in methanol, prior to reaction. 786 g of a 93.4% crude acid solution was obtained. The O,O-dimethyldithiophosphoric acid yield was 90.8%, based on phosphorus pentasulfide which underwent reaction. The phosphorus pentasulfide residue was 2.7 g (0.6%). As compared with Example 2, the yield was increased by 8.0%.

EXAMPLE 2d (Invention)

The procedure was as in Example 2, but 1.6 g of tetramethyl ammonium chloride was dissolved in methanol, prior to reaction. 804 g of a 95.1% crude acid solution was obtained. The O,O-dimethyldithiophosphoric acid yield was 95.2%, based on phosphorus pentasulfide which underwent reaction. The phosphorus pentasulfide residue was 0.5 g (0.1%). As compared with Example 2, the yield was increased by 12.4%.

EXAMPLE 3

(Without catalyst)

111 g of phosphorus pentasulfide was suspended in 40 g of O,O-diethyldithiophosphoric acid (85.3%) and the suspension was reacted within 2 hours at 70° C. with 92 g of ethanol. The reaction solution was maintained for 30 minutes at 70° C., for post-reaction. Next, the whole was cooled to room temperature, residual $H_2S$ was expelled by means of nitrogen, and filtered. 213 g of an 87.4% crude acid solution was obtained. The O,O-diethyldithiophosphoric acid yield was 84.9%, based on phosphorus pentasulfide which underwent reaction. The phosphorus pentasulfide residue was 4.2 g (3.8%).

EXAMPLE 3a (Invention)

The procedure was as in Example 3, but 0.22 g of trimethyldodecylphosphonium bromide was dissolved in ethanol, prior to reaction. 223 g of a 94.3% crude acid solution was obtained. The O,O-diethyldithiophosphoric acid yield was 94.9%, based on phosphorus pentasulfide which underwent reaction. The phosphorus pentasulfide residue was 0.4 g (0.4%). As compared with Example 3, the yield was increased by 10.0%.

EXAMPLE 4

(Without catalyst)

222 g of phosphorus pentasulfide was suspended in 70 g of O,O-diisopropyldithiophosphoric acid (92.6%) and the suspension was reacted with agitation within 2 hours with 240 g of isopropanol at 75° C. The whole was allowed to undergo postreaction for 1 h, then cooled to room temperature, residual $H_2S$ was expelled by means of nitrogen, and filtered. 481 g of an 88.3% crude acid solution was obtained. The O,O-diisopropyldithiophosphoric acid yield was 87.8%, based on phosphorus pentasulfide which underwent reaction. The phosphorus pentasulfide residue was 9.5 g (4.3%).

EXAMPLE 4a (Invention)

The procedure was as in Example 4, but 0.5 g of trimethylphosphine oxide was dissolved in isopropanol, prior to reaction. 504 g of a 94.9% crude acid solution was obtained. The O,O-diisopropyldithiophosphoric acid yield was 96.6%, based on phosphorus pentasulfide which underwent reaction. The phosphorus pentasulfide residue was 0.4 g (0.2%). As compared with Example 4, the yield was increased by 8.3%

EXAMPLE 4b (Invention)

The procedure was as in Example 4, but 0.34 g of tetrabutylphosphonium bromide was dissolved in isopropanol, prior to reaction. 504 g of a 96.7% crude acid solution was obtained. The O,O-diisopropyldithiophosphoric acid yield was 98.7%, based on phosphorus pentasulfide which underwent reaction. The phosphorus pentasulfide residue was 0.1 g (0.05%). As compared with Example 4, the yield was increased by 10.9%.

EXAMPLE 5

(Without catalyst)

A suspension of 666 g of phosphorus pentasulfide in 208 g of O,O-diisobutyldithiophosphoric acid (87%) was admixed with agitation at 80° C. within 2 hours with 888 g of iso-butanol. The whole was allowed to undergo post-reaction for 10 minutes and then cooled to room temperature. Residual $H_2S$ was expelled by means of nitrogen and the whole was filtered. 1625 g of an 84.8% crude acid solution was obtained. The O,O-diisobutyldithiophosphoric acid yield was 86.4%, based on phosphorus pentasulfide which underwent reaction. The phosphorus pentasulfide residue was 31.8 g (4.8%).

EXAMPLE 5a (Invention)

The procedure was as in Example 5, but 1.0 g of tetrabutylphosphonium bromide was dissolved in isobutanol, prior to reaction. 1661 g of a 96.0% crude acid solution was obtained. The O,O-diisobutyldithiophosphoric acid yield was 97.5%, based on phosphorus pentasulfide which underwent reaction. The phosphorus pentasulfide residue was 1.3 g (0.2%). As compared with Example 5, the yield was increased by 11.1%.

EXAMPLE 6

(Without catalyst)

A suspension of 444 g of phosphorus pentasulfide in 131 g of O,O-di-2-ethylhexyldithiophosphoric acid (92.1%) was admixed with agitation, within 2 hours at 80° C. with 1040 g of 2-ethylhexanol. After a 30 min. post-reaction period, the whole was cooled to room temperature, residual $H_2S$ was expelled by means of nitrogen, and the whole was filtered. 1420 g of 79.7% crude acid solution was obtained. The O,O-di-2-ethylhexyldithiophosphoric acid yield was 87.1%, based on phosphorus pentasulfide which underwent reaction. The phosphorus pentasulfide residue was 80.8 g (18.2%).

EXAMPLE 6a (Invention)

The procedure was as in Example 6, but 1.36 g of tetrabutylphosphonium bromide was dissolved in 2-ethylhexanol, prior to reaction. 1540 g of a 95.7% crude acid solution was obtained. The O,O-di-2-ethylhexyldithiophosphoric acid yield was 95.7%. The phosphorus pentasulfide residue was 0.5 g (0.1%). As compared with Example 6, the yield was increased by 8.6%.

EXAMPLE 7

(Without catalyst)

A suspension of 222 g of phosphorus pentasulfide in 80 g of n-octanol was admixed at 80° C. within 2 h with a further 440 g of n-octanol. The solution was maintained for 30 minutes at 80° C., for post-reaction. Next, the whole was cooled to room temperature, residual $H_2S$ was expelled by means of nitrogen, and the whole was filtered. 672 g of an 81.6% crude acid solution was obtained. The O,O-di-n-octyldithiophosphoric acid yield was 86.9%, based on phosphorus pentasulfide which underwent reaction. The phosphorus pentasulfide residue was 24.2 g (10.9%).

EXAMPLE 7a (Invention)

The procedure was as in Example 7, but 0.68 g of tetrabutylphosphonium bromide was dissolved in n-octanol, prior to reaction. 706 g of a 97.8% crude acid solution was obtained. The O,O-di-n-octyldithiophosphoric acid yield was 97.7%, based on phosphorus pentasulfide which underwent reaction. The phosphorus pentasulfide residue was 0.8 g (0.4%). As compared with Example 7, the yield was increased by 10.8%.

EXAMPLE 8

(Without catalyst)

A suspension of 55.5 g of phosphorus pentasulfide in 33 g of n-dodecanol was admixed at 80° C. within 2 hours with a further 153 g of dodecanol. A heatable dropping funnel was used to prevent the alcohol from solidifying. The solution was maintained for 30 minutes at 80° C., for post-reaction. Next, the whole was cooled to room temperature, residual $H_2S$ was expelled by means of nitrogen and the whole was filtered. 223 g of an 80.9% crude acid solution was obtained. The O,O-di-n-dodecyldithiophosphoric acid yield was 88.8%, based on phosphorus pentasulfide which underwent reaction. The phosphorus pentasulfide residue was 7.2 g (13.0%).

EXAMPLE 8a (Invention)

The procedure was as in Example 8, but 0.47 g of tetrabutylphosphonium bromide was dissolved in n-dodecanol, prior to reaction 232 g of a 95.0% crude acid solution was obtained. The O,O-di-n-dodecyldithiophosphoric acid yield was 95.1%, based on phosphorus pentasulfide which underwent reaction. The phosphorus pentasulfide residue was 0.4 g (0.7%). As compared with Example 8, the yield was increased by 6.3%.

EXAMPLE 9

(Without catalyst)

A suspension of 55.5 g of phosphorus pentasulfide in 40 g of n-octadecanol was admixed at 80° C. within 2 h with a further 230 g of n-octadecanol. A heatable dropping funnel was used to prevent the alcohol from solidifying. The solution was maintained for 30 minutes at 80° C., for post-reaction. Next, the whole was cooled to room temperature, residual $H_2S$ was expelled by means of nitrogen, and the whole was filtered. 306 g of a 78.8% crude acid solution was obtained. The O,O-di-n-octadecyldithiophosphoric acid yield was 89.7%, based on phosphorus pentasulfide which underwent reaction. The phosphorus pentasulfide residue was 8.5 g (15.3%).

EXAMPLE 9a (Invention)

The procedure was as in Example 9, but 0.63 g of tetraoctylphosphoniumchloride was dissolved in n-octadecanol. 314 g of a 94.4% crude acid solution was obtained. The O,O-di-n-octadecyldithiophosphoric acid yield was 95.1%, based on phosphorus pentasulfide which underwent reaction. The phosphorus pentasulfide residue was 1.0 g (1.8%). As compared with Example 8, the yield was increased by 5.4%.

EXAMPLE 10

(Without catalyst)

188 g of phenol was admixed with agitation, at 80° to 85° C. and within 10 minutes, with 111 g of phosphorus pentasulfide. Next, the reaction mixture was heated for 50 minutes to 90° C., filtered while hot and residual $H_2S$ was expelled at 65° C. by means of nitrogen. 235 g of a 60.5% crude acid solution was obtained. The O,O-diphenyldithiophosphoric acid yield was 93.2%, based on phosphorus pentasulfide which underwent reaction. The phosphorus pentasulfide residue was 51 g (45.9%).

EXAMPLE 10a (Invention)

The procedure was as in Example 10, but 0.42 g of ethyl-trioctylphosphonium bromide was added to the phenol, prior to reaction. 281 g of a 98.4% crude acid solution was obtained. The O,O-diphenyldithiophosphoric acid yield was 98.0%, based on phosphorus pentasulfide which underwent reaction. The phosphorus pentasulfide residue was 0.02 g (0.02%). As compared with Example 10, the yield was increased by 4.8%.

EXAMPLE 11

(Comparative Example with the use of pyridine as the catalyst)

111 g of phosphorus pentasulfide was suspended in 35 ml of toluene and the suspension was reacted within 2 h at 60° C. with 64 g of methanol which contained 0.6 g of pyridine. The solution was maintained for 30 minutes at 60° C., for post-reaction. Next, the whole was cooled, residual $H_2S$ was expelled by means of nitrogen, and the whole was filtered. 181.5 g of a 75.6% crude acid solution in toluene was obtained. The O,O-dimethyldithiophosphoric acid yield was 87.2%, based on phosphorus pentasulfide which underwent reaction. The phosphorus pentasulfide residue was 0.65 g (0.6%).

EXAMPLE 12

(Comparative Example with the use of urea as the catalyst).

The procedure was as in Example 11, but 0.6 g of urea was dissolved in methanol, prior to reaction. 179 g of a 76.3% crude acid solution in toluene was obtained. The O,O-dimethyldithiophosphoric acid yield was 88.3%, based on phosphorus pentasulfide which underwent reaction. The phosphorus pentasulfide residue was 2.5 g (2.3%).

EXAMPLE 13

(Comparative Example with the use of ammonia as the catalyst)

The procedure was as in Example 11, but 2 mg of $NH_3$ was dissolved in methanol, prior to reaction, 168 g of a 70.2% crude acid solution in toluene was obtained. The O,O-dimethyldithiophosphoric acid yield was 78.1%, based on phosphorus pentasulfide which under-

| Example | Alcohol | Catalyst* | Suspension in | Acid content | Penta residue | yield** |
|---|---|---|---|---|---|---|
| 1 | Methanol | — | toluene | 74.9% | 1.6% | 86.8% |
| 1 a | Methanol | 0.05% $(CH_3)_4PCl$ | toluene | 81.3% | 0.1% | 95.1% |
| 1 b | Methanol | 0.15% $(C_8H_{17})_3PO$ | toluene | 80.0% | 0.3% | 93.7% |
| 1 c | Methanol | 0.29% $(C_4H_9)_4NI$ | toluene | 81.1% | 0.2% | 95.2% |
| 2 | Methanol | — | crude acid | 86.7% | 2.7% | 82.8% |
| 2 a | Methanol | 0.26% $(C_4H_9)_4PBr$ | crude acid | 96.0% | 0.3% | 95.4% |
| 2 b | Methanol | 0.62% $(CH_3)_3PS$ | crude acid | 92.8% | 1.4% | 90.5% |
| 2 c | Methanol | 0.62% $(CH_3)_2P(=S)(S)Na$ | crude acid | 93.4% | 0.6% | 90.8% |
| 2 d | Methanol | 0.62% $(CH_3)_4NCl$ | crude acid | 95.1% | 0.1% | 95.2% |
| 3 | Ethanol | — | crude acid | 87.4% | 3.8% | 84.9% |
| 3 a | Ethanol | 0.24% $(CH_3)_3C_{12}H_{25}PBr$ | crude acid | 94.3% | 0.4% | 94.9% |
| 4 | iso-Propanol | — | crude acid | 88.3% | 4.3% | 87.8% |
| 4 a | iso-Propanol | 0.21% $(CH_3)_3PO$ | crude acid | 94.9% | 0.2% | 96.6% |
| 4 b | iso-Propanol | 0.14% $(C_4H_9)_4PBr$ | crude acid | 96.7% | 0.05% | 98.7% |
| 5 | iso-Butanol | — | crude acid | 84.8% | 4.8% | 86.4% |
| 5 a | iso-Butanol | 0.11% $(C_4H_9)_4PBr$ | crude acid | 96.0% | 0.2% | 97.5% |
| 6 | 2-Ethylhexanol | — | crude acid | 79.7% | 18.2% | 87.1% |
| 6 a | 2-Ethylhexanol | 0.13% $(C_4H_9)_4PBr$ | crude acid | 95.7% | 0.1% | 95.7% |
| 7 | n-Octanol | — | n-Octanol | 81.6% | 10.9% | 86.9% |
| 7 a | n-Octanol | 0.13% $(C_4H_9)_4PBr$ | n-Octanol | 97.8% | 0.4% | 97.7% |
| 8 | n-Dodecanol | — | n-Dodecanol | 80.9% | 13.0% | 88.8% |
| 8 a | n-Dodecanol | 0.25% $(C_4H_9)_4PBr$ | n-Dodecanol | 95.0% | 0.7% | 95.1% |
| 9 | n-Octadecanol | — | n-Octadecanol | 78.8% | 15.3% | 89.7% |
| 9 a | n-Octadecanol | 0.23% $(C_8H_{17})_4PCl$ | n-Octadecanol | 94.4% | 1.8% | 95.1% |
| 10 | Phenol | — | Phenol | 60.5% | 45.9% | 93.2% |
| 10 a | Phenol | 0.22% $(C_2H_5)(C_8H_{17})_3PBr$ | Phenol | 98.4% | 0.02% | 98.0% |

*wgt %, based on alcohol
**based on phosphorus pentasulfide reacted went reaction. The phosphorus pentasulfide residue was 5.0 g (4.5%)

EXAMPLE 14

(Invention)

The procedure was as in Example 11, but 0.17 g of $(C_4H_9)_4PBr$ was dissolved in methanol, prior to reaction. 184 g of an 81.8% crude acid solution in toluene was obtained. The O,O-dimethyldithiophosphoric acid yield was 95.6%, based on phosphorus pentasulfide which underwent reaction. The phosphorus pentasulfide residue was 0.6 g (0.5%). As compared with Example 11, Example 12 and Example 13, respectively, the yield was increased by 8.4%, 7.3% and 17.5%, respectively.

EXAMPLE 15

(Comparative Example; alkyl-arylester)

A suspension of 111 g of phosphorus pentasulfide in 35 ml of toluene was admixed dropwise within 1 hour at 90° C. with a mixture of 94 g of phenol and 130 g of n-octanol. After a post-reaction period of 15 minutes, the whole was cooled to room temperature, residual $H_2S$ was expelled by means of nitrogen, and the whole was filtered. 264 g of crude acid was obtained. In the $^{31}P$-NMR-spectrum, it was found to contain
94 mol % of O,O-di-n-octyldithiophosphoric acid,
6 mol % of O,O-diphenyldithiophosphoric acid, and
0 mol % of O-n-octyl-O-phenyldithiophosphoric acid.
The acid number (mg KOH/g substance) was 71 (theoretical value for complete reaction: 161). The phosphorus pentasulfide residue was 66.0 g (59.5%).

EXAMPLE 16

(Invention)

The procedure was as in Example 15, but 0.56 g of ethyltrioctylphosphonium bromide was dissolved in the n-octanol/phenol-mixture, prior to reaction. 344 g of crude acid was obtained. In the $^{31}P$-NMR-spectrum, it was found to contain
25 mol % of O,O-di-n-octyldithiophosphoric acid,
25 mol % of O,O-diphenyldithiophosphoric acid and
50 mol % of O-n-octyl-O-phenyldithiophosphoric acid.
The acid number (mg KOH/g substance) was 156 (theoretical value for complete reaction: 161). The phosphorus pentasulfide residue was 0.5 g (0.5%).

We claim:

1. In the process for reacting an alcohol and/or phenol with phosphorus pentasulfide in the presence of a catalyst, the improvement which comprises using, as the catalyst, compounds selected from the group consisting of:

(a) phosphonium salts of the general formula

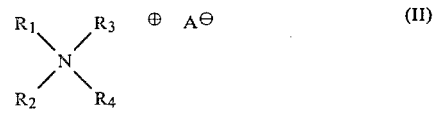

or (b) ammonium salts of the general formula

or (c) phosphine oxides of the general formula

or (d) phosphine sulfides of the general formula $$\begin{array}{c} R_1 \\ \phantom{R_2-}\diagdown \\ R_2-P=S \\ \phantom{R_2-}\diagup \\ R_3 \end{array} \quad (IV)$$

or (e) phosphinic acid derivatives of the general formula

in which formulae I through V the substituents $R_1$, $R_2$, $R_3$, and $R_4$ each stand for identical or different alkyl-, aryl-, alkaryl- or aralkyl-groups having from 1 to 22 carbon atoms, A stands for an acid radical of a hydrohalic acid, sulfuric acid, nitric acid, acetic acid or dialkyldithiophosphoric acid and X and Y, respectively, stand for both oxygen and sulfur, and M stands for a monovalent metal or hydrogen; and using the said compounds in a proportion of 0.001 to 5 weight %, based on the alcohol or phenol.

2. Process as claimed in claim 1, wherein catalysts of the general formulae I through V are used, in which $R_1$, $R_2$, $R_3$ and $R_4$ each stand for identical or different alkyl groups having from 1 to 12 carbon atoms.

* * * * *